(12) United States Patent  (10) Patent No.: US 8,399,698 B1
Gherardi et al.  (45) Date of Patent: Mar. 19, 2013

(54) SUBSTITUTED ACTIVATED METHYLENE REAGENTS AND METHODS OF USING SUCH REAGENTS TO FORM ELECTRON DEFICIENT OLEFINS

(75) Inventors: Stefano Gherardi, Dublin (IE); Ciaran B. McArdle, Dublin (IE); Giovanni Faimani, Dublin (IE); Christoph Loschen, Duesseldorf (DE)

(73) Assignee: Henkel Ireland Limited, Monheim (DE)

( * ) Notice: Subject to any disclaimer, the term of this patent is extended or adjusted under 35 U.S.C. 154(b) by 318 days.

(21) Appl. No.: 12/604,035

(22) Filed: Oct. 22, 2009

Related U.S. Application Data (60) Provisional application No. 61/108,242, filed on Oct. 24, 2008.

(51) Int. Cl.
*C07C 69/52* (2006.01)
*C07C 57/02* (2006.01)
(52) U.S. Cl. ........................................ 560/205; 562/598
(58) Field of Classification Search .................. None
See application file for complete search history.

(56) References Cited

U.S. PATENT DOCUMENTS

| | | |
|---|---|---|
| 2,363,464 A | 11/1944 | Senkus |
| 2,413,249 A | 12/1946 | Senkus |
| 2,413,250 A | 12/1946 | Senkus |
| 2,415,046 A | 1/1947 | Senkus |
| 2,582,128 A | 1/1952 | Hurwitz |
| 2,721,858 A | 10/1955 | Joyner et al. |
| 2,756,251 A | 7/1956 | Joyner et al. |
| 2,763,677 A | 9/1956 | Jeremias |
| 2,870,193 A | 1/1959 | Pollack et al. |
| 3,048,615 A | 8/1962 | Fields |
| 3,142,698 A | 7/1964 | Halpern et al. |
| 3,282,773 A | 11/1966 | Wicker |
| 3,554,987 A | 1/1971 | Smith |
| 3,903,055 A | 9/1975 | Buck |
| 3,975,422 A | 8/1976 | Buck |
| 3,988,299 A | 10/1976 | Malofsky |
| 3,995,641 A | 12/1976 | Kronenthal et al. |
| 4,003,942 A | 1/1977 | Buck |
| 4,012,402 A | 3/1977 | Buck |
| 4,013,703 A | 3/1977 | Buck |
| 4,056,543 A | 11/1977 | Ponticello |
| 4,160,864 A | 7/1979 | Ponticello et al. |
| 4,202,920 A | 5/1980 | Renner et al. |
| 4,364,876 A | 12/1982 | Kimura et al. |
| 4,440,910 A | 4/1984 | O'Connor |
| 4,512,357 A | 4/1985 | Earl |
| 4,556,700 A | 12/1985 | Harris et al. |
| 4,560,723 A | 12/1985 | Millet |

(Continued)

FOREIGN PATENT DOCUMENTS

| | | |
|---|---|---|
| DE | 2 626 173 | 12/1977 |
| DE | 40 34 080 A1 | 6/1991 |

(Continued)

OTHER PUBLICATIONS

Database CAPLUS Chemical Abstracts Service, Columbus, Ohio, US; Database Accession No. 1975:17074, Abstract of Dardenne et al., Phytochemistry (Elsevier) (1974), 13(10), 2195-9.*

(Continued)

*Primary Examiner* — Karl J Puttlitz
(74) *Attorney, Agent, or Firm* — Steven C. Bauman (57) ABSTRACT

This invention relates to substituted activated methylene reagents and methods of using such reagents to form electron deficient olefins such as butadienes.

12 Claims, 5 Drawing Sheets

U.S. PATENT DOCUMENTS

| | | | |
|---|---|---|---|
| 4,587,059 | A | 5/1986 | Harth et al. |
| 4,622,414 | A | 11/1986 | McKervey |
| 4,636,539 | A | 1/1987 | Harris et al. |
| 4,695,615 | A | 9/1987 | Leonard et al. |
| 4,718,966 | A | 1/1988 | Harris et al. |
| 4,764,545 | A | 8/1988 | Yosida |
| 4,837,260 | A | 6/1989 | Sato et al. |
| 4,855,461 | A | 8/1989 | Harris |
| 4,876,045 | A | 10/1989 | Longo et al. |
| 4,906,317 | A | 3/1990 | Liu |
| 5,142,098 | A | 8/1992 | Bru-Magniez et al. |
| 5,288,794 | A | 2/1994 | Attarwala |
| 5,306,752 | A | 4/1994 | Attarwala |
| 5,312,864 | A | 5/1994 | Wenz et al. |
| 5,328,944 | A | 7/1994 | Attarwala et al. |
| 5,340,873 | A | 8/1994 | Mitry |
| 5,386,047 | A | 1/1995 | Nakos et al. |
| 5,424,343 | A | 6/1995 | Attarwala |
| 5,424,344 | A | 6/1995 | Lewin |
| 5,455,369 | A | 10/1995 | Meier et al. |
| 5,624,699 | A | 4/1997 | Lang |
| 5,703,267 | A | 12/1997 | Takahashi et al. |
| 5,744,642 | A | 4/1998 | Lantzsch et al. |
| 5,994,464 | A | 11/1999 | Ohsawa et al. |
| 6,093,780 | A | 7/2000 | Attarwala |
| 6,096,848 | A | 8/2000 | Gololobov et al. |
| 6,174,919 | B1 | 1/2001 | Hickey |
| 6,245,933 | B1 | 6/2001 | Malofsky et al. |
| 6,291,544 | B1 | 9/2001 | Kotzev |
| 6,531,460 | B1 | 3/2003 | Takenouchi et al. |
| 6,833,196 | B1 | 12/2004 | Wojciak |
| 6,835,789 | B1 | 12/2004 | Kneafsey et al. |
| 2006/0094833 | A1 | 5/2006 | McDonnell et al. |
| 2006/0269870 | A1 | 11/2006 | Harada et al. |
| 2008/0241249 | A1 | 10/2008 | Quintero et al. |

FOREIGN PATENT DOCUMENTS

| | | |
|---|---|---|
| DE | 19519958 | 12/1995 |
| EP | 0 127 855 | 12/1984 |
| EP | 0 267 981 A | 5/1988 |
| EP | 0 459 617 | 12/1991 |
| WO | WO 94/15590 A1 | 7/1994 |
| WO | WO 94/15907 | 7/1994 |
| WO | WO 95/32183 | 11/1995 |
| WO | WO 99/14206 A1 | 3/1999 |
| WO | WO 03/006225 A1 | 1/2003 |
| WO | WO 03/086805 A2 | 10/2003 |

OTHER PUBLICATIONS

Carl J. Buck, Unequivocal Synthesis of Bis(2-Cyanoacrylate) Monomers, I. Via Anthracene Adducts, *Journal of Polymer Science, Polymer Chemistry Edition*, vol. 16, 2475-507 (1978).
G. Jones, "The Knoevenagle Condensation", *Organic Reactions*, vol. XV, 204, Wiley New York (1987).
F. Bigi et al., "Montmorillonite KSF as an Inorganic, Water Stable, and Reusable Catalyst for the Knoevenagel Synthesis of Coumarin-3-carboxylic Acids", Journal Organic Chemistry, vol. 64, 1033-35 (1999).
B. Green et al., Synthesis of Steroidal 16, 17-Fused Unsaturated δ-Lactones[1], *Journal Organic Chemistry*, vol. 50, 640-44 (1985).
P. Rao et al., "Zinc Chloride as a New Catalyst for Knoevenagel Condensation" *Tetrahedron Letters*, vol. 32, No. 41, 5821-22 (1991).
J. S. Yadav et al., "Phosphane-Catalyzed Knoevenagel Condensation: A Facile Synthesis of Cyanoacrylates and α-Cyanonitriles", *European Journal Organic Chemistry*, 546-51 (2004).
L. Tietze et al., Comprehensive Organic Synthesis, Pergamon Press, Oxford, vol. 2, Chapter 1.11, 341 (1991).
P. Laszlo, "Catalysis of Organic Reactions by Inorganic Solids", *Accounts of Chemical Research*, vol. 19, 121-27 (1986).
K. Kloestra et al., "Base and Acid Catalysis by the Alkali-containing MCM-41 Mesoporous Molecular Sieve", *Journal Chemical Soc. Chem. Commun.*, 1005-06 (1995).
P. Lednor et al., "The Use of a High Surface Area Silicon Oxynitride as a Solid, Basic Catalyst", Journal Chemical Society, Chem. Commun., 1625-26 (1991).
F. Bigi et al., "A Revision of the Biginelli Reaction Under Solid Acid Catalysis. Solvent-free Synthesis of Dihydropyrimidines Over Montmorillonite KSF" *Tetrahedron Letters*, vol. 40, 3465-68.
F. Bigi et al., "Clean synthesis in water: uncatalysed preparation of ylidenemalononitriles", *Green R. Chemistry*, vol. 2, 101-03 (2000).
R. Breslow, "Hydrophobic Effects on Simple Organic Reactions in Water", *Accounts of Chemical Research*, vol. 24, 159-64 (1991).
C. Li, "Organic Reactions in Aqueous Media—With a Focus on Carbon-Carbon Bond Formation", *Chemical Reviews*, vol. 93, 2023-35 (1993).
T. Welton, "Room Temperature Ionic Liquids. Solvents for Synthesis and Catalysis", *Chemical Reviews*. vol. 99, 2071-83 (1999).
D. Morrison et al., "Base-promoted reactions in ionic liquid solvents. The Knoevenagel and Robinson annulation", *Tetrahedron Letters*. vol. 42, 6053-55 (2001).
Fraga-Dubreiul et al., "Grafted Ionic liquid-phase-supported synthesis of small organic molecules", *Tetrahedron Letter*, vol. 42, 6097-6100 (2001).
M. Smietana et al., "Preparation of Silyl Enol Ethers Using (Bistrimethylsilyl)acetamide in Ionic liquids", *Organic Letters*, vol. 3, No. 7, 1037-39 (2001).
Li et al., "n-Butyl Pyridinium Nitrate as a Reusable Ionic Liquid Medium for Knoevenagel Condensation", *Chinese Chemical Letters*, vol. 14, No. 5, 448-50 (2003).
J. Harjani et al., "Lewis acidic ionic liquids for the synthesis of electrophilic alkenes via the Knoevenagel condensation" *Tetrahedron Letters*, vol. 43, 1127-30 (2002).
Xu et al,, "Knoevenagel condensation Reaction Catalyzed by Functionalized Ionic Liquid 1-(2-Hydroxyethyl)-3-methyl Imidazolium Chloride", *Chinese Journal of Organic Chemistry*, vol. 24(10), 1253-56 (2004).
Su et al., "Organic Reactions in Ionic Liquids: Knoevenagel Condensation Catalyzed by Ethylenediammonium Diacelate", *Synthesis 2003*, No. 4, 555-59 (2003).
Moehrle et al., "Aminomethylierung von 1,3-Diketonen" *Pharmazie*, vol. 40, 697-701 (1985).
J. March, "Reactions" *Advanced Organic Chemistry*, 3$^{rd}$ Edition, Wiley & Sons Inc., 417 (1985).
J. March, "Addition to Carbon-Hetero Multiple Bonds", *Advanced Organic Chemistry*, 3$^{rd}$ Edition, Wiley & Sons, 802-03 (1985).
M. B. Smith, *Organic Synthesis*, McGraw Hill International Chemistry Series, 1302 (1994).
Tehrani et al., "Product Class 8: Iminium Salts", *Science of Synthesis*. vol. 27, 313-48 (2004).
B. Hin et al., "Facile Synthesis of α-Substituted Acrylate Esters", *Journal of Organic Chemistry*, vol. 67, 7365-68 (2002).
Holy et al., "The Mannich Reaction-II Derivatization of Aldehydes and Ketones Using Dimethyl(methylene)ammonium Salts", *Tetrahedron Letters*, vol. 35, 613-19 (1979).
Bryson et al., "Preformed Mannich Salts: A Facile Preparation of Dimethyl(methylene)ammonium Iodide", *Journal of Organic Chemistry*, vol. 45, 524-25 (1980)
J. March, "The Pinacol Rearrangement", *Advanced Organic Chemistry*, 3$^{rd}$ Edition, Wiley & Sons, 963-64 (1985).
J. March, "Free-Radical Substitution", *Advanced Organic Chemistry*, 3$^{rd}$ Edition, Wiley & Sons, 642 (1985).
Jahn et al., "A Novel and Simple Method for the Preparation of Iminium Salts", *Tetrahedron Letters*, vol. 34, No. 37, 5863-66 (1993.
R. J. Vijin et al., Synthesis, 573 (1994).
Davis, "Chemistry Letters", vol. 33, Issue 9, 1072-77 (2004).
Davis et al., "Ionic Liquids in Sythesis", P. Wassercheid and T. Welton, eds., Wiley-VCH Verlag GmbH & Co. KgaA, Chapter 2 (2003).
M.G. Djamali, P. Burba, K.H. Lieser, "Synthesis und Eigenschaften eines Celluloseuastauschers mit Diaminodibenzo-18-Krone-6 als Ankergruppe", Die Angewandte Makromolecular Chemie, vol. 92, 145-54 (1980).
K. Babic, "Reactive and Functional Polymers", vol. 66, 1494-1505 (2006).
Trumbo et al., "Copolmerization Behavior of 3-Isopropenyl-α, α-Dimethylbenzylamine and a Preliminary Evaluation of the Copolymers in Thermoset Coatings", *Journal of Applied Polymer Science*. vol. 82, 1030-39 (2001).

T. Giesenberg et al., "Synthesis and Functionalization of a New Kind of Silica Particle." *Agnew. Int. Chem. Int. Ed.*, 43, 5697-5700 (2004).

Zhang et al. "An Investigation of Knoevenagel condensation reaction in microreactors using a new zeolite catalyst", *Applied Catalysis A: General*, 261, 109-118 (2004).

Mehnert et al., "Chemical Communications", 3010 (2002).

Lee and Lee, "Bulletin of the Korean Chemical Society", vol. 25, Issue 10, 1531-37 (2004).

H. R. Synder and W. E. Hamlin, "Alkylation of Nitroparaffins with Amines and Their Derivatives", *Journal of American Chemical Society*, vol. 72, 5082-85 (1950).

H. G. Johnson, "Reaction of Aliphatic Amines with Formaldehyde and Nitroparaffins. II. Secondary Amines", *Journal of American Chermical Society*, vol. 68, 12-14 (1946).

M. Semkus, "Journal of the American Chemical Society", vol. 68, 10-12 (1946).

Sarac, "Progress in Polymer Science", vol. 24, 1149-1201 (1999).

Brough et al., "Pyrimidinyl Nitronyl Nitroxides", *Chemical European Journal*, vol. 12, 5134 (2006).

Zhou et al., *J. Polym. Sci., Part A Polym. Chem. Ed.*, 29, 1097 (1991).

Mehrotra et al., "Journal of Organometalic Chemistry", vol. 24, 811-21 (1970).

Son et al., "Synthesis of Hexahydro-3,3,5,5,7-pentaalkyl-2H-1,4-diazepin-2-ones from 1,3-Diamines and Ketones", *J. Org. Chem.*, vol. 46, 323 (1981).

Senkus, Acetals of Nitro Alcohols and Corresponding Amino Acetals, *J. Amer. Chem. Soc.*, vol. 69, 1380-81 (1947).

Renner et al., "Cure of Epoxy Resins with Esters of Cyanoacrylic Acid", *Journal of Polymer Science: Polymer Chemistry Edition*, vol. 23, 2341 (1985).

Kennedy et al., "Macromers by Carbocationic Polymerization. X. Synthesis, Characterization, and Polymerizability of Cyanoacrylate-Capped Polyisobutylenes", *Journal of Macromolecular Science, Part A*, 28:2, 209-24 (1991).

Khrustalev et al., "Synthesis and X-ray structural study of 1-adamantylmethy 2-cyanoacrylatel and 1,10-decanediol bis-2-cyanoacrylate", *Russian Chemical Bulletin*, vol. 45, No. 9, 2172 (1996).

Y. Gololobov et al., "A Novel approach to the synthesis of bis(2-cyanoacrylates)", *Russian Chemical Bulletin*, vol. 42, No. 5, 961 (1993).

Y. Gololobov et al., "Synthesis of bis(2-cyanoacrylates) from 2-cyanoacryloyl chloride and 2-butene-and-2-butyne-1,4-diols", *Russian Chemical Bulletin*, vol. 44, No. 4, 760 (1995).

J.-L. De Keyser et al., "A Versatile and Convenient Multigram Sythesis of Methylidenemalonic Acid Diesters", *J. Org. Chem.*, vol. 53, 4859 (1988).

Vijayalakshimi et al., "Alkyl and substituted alkyl 2-cyanoacrylates. Part I. Sythesis and Properties", *J. Adhesion Science Technology*, vol. 4, No. 9. 733 (1990).

Guseva et al., "Organic Chemistry. Sythesis of functionality substituted cyanoacetates." *Russian Chemical Bulletin*, vol. 42, No. 3, 478 (1993).

Guseva et al., "Organic Chemistry" *Russian Chemical Bulletin*, vol. 43, No. 4, 595 (1995).

Gololobov and Gruber, Russian Chemical Review, vol. 66, Issue 11, 953 (1997).

Senchenya et al., "Silicon-containing esters of α-cyanoacrylic acid: synthesis and properties" *Russian Chemical Bulletin*, vol. 42, No. 5, 909 (1993).

Bowie J. H. et al., "Tetrahedron", vol. 23, 305-20 (1967).

J. S. Norwick et al., J. Org. Chem., 57(28), 7364-66 (1992).

International Search Report for International Patent Application No. PCT/EP2006/064489 dated Dec. 30, 2008.

International Search Report for International Patent Application No. PCT/EP2008/064490 dated May 4, 2009.

International Search Report for International Application No. PCT/EP2008/064488 dated Jul. 16, 2009.

H.C. Haas, et al., "Carbamylmethyl Esthers of Unsaturated Acids", Journal of Polymer Science; vol. XXXVII, Issue 131; pp. 217-319, 1959, (XP002518680).

J.L. De Keyser et al., "A Versatile and convenient multigram synthesis of methylidenamalonic acid diesters", J. Org. Chem., pp. 4859-48562, (1988) (XP002518681).

D.A. Aronovich, et al.; J. Appl. Chem. USSR; vol. 52, pp. 900-902; 1979 (XP002518682).

X. Yang; Organic Preparations and Procedures International; vol. 30, No. 2; pp. 239-242; 1998 (XP002518684).

P.H. Mason, et al., "A New Route to Subsituted Glutaric Acid Derivatives from Allylic Malonates"; Synthetic Communications; vol. 25(2); pp. 183-190; 1995.

T. Sato, et al., "Synthesis of Cooper(II) Chelate of ethyl a-(acetoacetoxymethyl)acrylate and its Radical-initiated Polymerization"; Makromol. Chem., Rapid Commun. vol. 11; pp. 553-557; 1990.

M.L. Meketa, et al., "An Efficacious Method for the Halogenation of .beta.-dicarbonyl Compounds Under Mildly Acidic Condtions"; Tetrahedron Letter; vol. 46(28); pp. 4749-4751; 2005; XP002520970.

M.L. Meketa, et al., "An Efficacious Method for the Halogenation of .beta.-dicarbonyl Compounds Under Mildly Acidic Conditions"; Tetrahedron Letter, vol. 46(28); pp. 4749-4751; 2005, XP002520971.

R.C. Cookson, et al., "2-Phenylthioallyl Alcohols and their use in the Synthesis of 1,4-diketones and Cyclopentenones"; Journal of Chemical Society. Chemical Communications; (23); p. 990; 1976, XP002520969

P.H. Mason, et al., "Some Mechanistic and Synthetic Aspects of the DABCO Catalyzed Rearrangement of Allylic Esters"; Tetrahedron; vol. 50(41);pp. 12001-12008, XP002520967, 1994.

L.S. Boguslayskaya, et al., Journal of Organic Chemistry; vol. 9, pp. 295-299; 1793, XP002520972, 1973.

Samatha, et al., "Effect of Addition of Various Acrylates on the Performance of Ethyl Cyanoacrylate Adhesive", Polym.—Plast. Technol. Eng., 39(2), 381-92, (2000).

Vijayalakshmi, et al., "Synthesis and End Use of Evaluation of Pinene-Based Alicyclic Acrylates", *J. Polym. Mat.*, 13, pps. 127-131 (1996)

Yamada, et al., "Determination of Absolute Rate Constants for Radical Polymerization and Copolymerization of Ethyl a-Cyanoacrylate in the Presence of Effective Inhibitors against Anionic Polymerization", Makromol. Chem., 184, 1025 (1983).

Vijayalakshmi, et al., "Synthesis of 3-Substituted-2-cyanoacrylates: Their Evaluation as Cross-link in Cyanoacrylate Adhesive Compositions", J. Polym, Mat., 49, 1387 (1993).

Ponticello, "The Preparation of a-Substituted Acrylic Esters", *J. Polym. Sci., Polym. Chem. Edn.*, 17, pp. 3509-18 (1979).

Pines, Alul and Kolobieski, "Bromination Synthesis of a-Methylstyrene with N-Bromosuccinimide Synthesis of 2-Phenyl-1,5-hexadiene", *J. Org, Chem.*, 1113 (1957).

* cited by examiner

SUBSTITUTED ACTIVATED METHYLENE REAGENTS AND METHODS OF USING SUCH REAGENTS TO FORM ELECTRON DEFICIENT OLEFINS

CROSS REFERENCE TO RELATED APPLICATIONS

This application claims a priority filing date under 35 U.S.C. §119(e) from U.S. Provisional Application No. 61/108,242, filed Oct. 24, 2008, the disclosure of which is hereby expressly incorporated herein by reference.

BACKGROUND OF THE INVENTION

1. Field of the Invention

This invention relates to substituted activated methylene reagents and methods of using such reagents to form electron deficient olefins.

2. Brief Description of Related Technology

Fast curing adhesives are well known. Most of those types of adhesives are based on cyanoacrylate chemistry.

Cyanoacrylate adhesives are known for their fast adhesion and ability to bond a wide variety of substrates. They are marketed as "super glue" type adhesives. They are useful as an all-purpose adhesive since they are a single component adhesive, very economical as only a small amount will do, and generally do not require any equipment to effectuate curing.

Traditionally, cyanoacrylate monomers have been produced by way of a Knoevenagel condensation reaction between a formaldehyde precursor, such as paraformaldehyde, and an alkyl cyanoacetate (an activated methylene reagent) with a basic catalyst. During the reaction, cyanoacrylate monomer forms and polymerises in situ to a prepolymer. The prepolymer is subsequently thermally cracked or depolymerised, yielding cyanoacrylate monomer. This approach has remained essentially the same over time, though various improvements and variants have been introduced. See e.g. U.S. Pat. Nos. 6,245,933, 5,624,699, 4,364,876, 2,721,858, 2,763,677 and 2,756,251.

In U.S. Pat. No. 3,142,698, the synthesis of difunctional cyanoacrylates using a Knoevenagel condensation reaction is described. However, the ability to thermally depolymerise the resulting, now crosslinked, prepolymer in a reliable and reproducible manner to produce pure difunctional monomers in high yields is questionable [see J. Buck, *J. Polym. Sci., Polym. Chem. Ed.,* 16, 2475-2507 (1978), and U.S. Pat. Nos. 3,975,422, 3,903,055, 4,003,942, 4,012,402, and 4,013,703].

A variety of other processes for producing cyanoacrylate monomers are known, some of which are described below. For instance, U.S. Pat. No. 5,703,267 defines a process for producing a 2-cyanoacrylic acid which comprises subjecting a 2-cyanoacrylate and an organic acid to a transesterification reaction.

U.S. Pat. No. 5,455,369 defines an improvement in a process for preparing methyl cyanoacrylate, in which methyl cyanoacetate is reacted with formaldehyde to form a polymer that is then depolymerized to the monomeric product, and in which the purity of yield is reported to be 96% or better. The improvement of the '369 patent is reported to be conducting the process in a polyethylene glycol) diacetate, dipropionate, or dibutyrate, having a number average molecular weight of 200-400, as the solvent.

U.S. Pat. No. 6,096,848 defines a process for the production of a biscyanoacrylate, which comprises the steps of esterifying a 2-cyanoacrylic acid or transesterifying an alkyl ester thereof to obtain a reaction mixture; and fractionally crystallizing the reaction mixture to obtain the biscyanoacrylate.

U.S. Pat. No. 4,587,059 defines a process for the preparation of monomeric 2-cyanoacrylates comprising the steps of (a) reacting (i) a 2,4-dicyanoglutarate with (ii) formaldehyde, cyclic or linear polymers of formaldehyde, or a mixture thereof, in the presence of between about 0.5 and about 5 mols of water per mol of 2,4-dicyanoglutarate, at an acid pH of about 3 to slightly less than 7, and at a temperature of about 70 to about 140, to form an oligomeric intermediate product, and (b) removing water that is present from step (a) and thermolyzing the oligomeric intermediate product for a period of time sufficient to effect its conversion to monomeric 2-cyanoacrylates.

Commercial production of cyanoacrylate monomers ordinarily relies on the depolymerisation of a prepolymer formed under Knoevenagel condensation reaction conditions, as noted above. Still today the Knoevenagel condensation reaction is believed to remain the most efficient and prevalent commercial method for producing high yields of monofunctional cyanoacrylates. Nevertheless, it would be desirable to not have to resort to thermally induced depolymerisation of a prepolymer produced by the Knoevenagel condensation reaction. This prospect may also enable facile access to highly useful difunctional monomers, such as so-called bis-cyanaocrylates or hybrid materials of cyanoacrylate and other polymerisable or reactive functionality.

Vijayalakshmi et al., *J. Ad. Sci. Technol.,* 4, 9, 733 (1990) describes the synthesis of cyanoacetates and corresponding cyanoacrylates, including preparation from chloroacetic acid and its esters by subsequent reaction with sodium cyanide.

Guseva et al., *Russian Chem. Bull.,* 42, 3, 478 (1993) describes functionalized cyanoacetates, some of which were used in the subsequent synthesis of corresponding cyanoacrylates [Guseva et al., *Russian Chem. Bull.,* 43, 4, 595 (1994); see also Golobolov and Gruber, *Russian Chem. Rev.,* 66, 11, 953 (1997)].

One of the functionalized cyanoacetates noted in the preceding paragraph is glycidyl cyanoacetate. While the synthesis and characterisation of glycidyl cyanoacetate has been reported (such as is described in the preceding paragraph), the synthesis, characterisation and provision of performance characteristics of the corresponding glycidyl cyanoacrylate have not to date been published.

Other cyanoacetates are known, such as those with siliconised functionalities. See e.g. Senchenya et al., *Russian Chem. Bull.,* 42, 5, 909 (1993) and European Patent Document No. EP 0 459 617.

The preparation of mono-, di-, tri- and tetra-functional cyanoacetates as curatives for epoxy resins for adhesive applications has been described. See e.g. Renner et al., "Cure of Epoxy Resins with Esters of Cyanoacrylic Acid", *J. Polym. Sci., Polym. Chem. Ed.,* 23, 2341 (1985) and U.S. Pat. Nos. 4,202,920 and 4,512,357.

K-D. Ahn and H. K. Hall, "Synthesis and Polymerization of the Four 1,3-Di(cyano and/or Carbomethoxy)-Substituted Butadienes", *J. Polym. Sci.: Polym. Chem. Ed.,* 19, 629-44 (1981) is directed to the synthesis of 1,3-dielectronegatively substituted butadienes to ascertain their feasibility for use as monomers in radical and/or anionic polymerizations. Ahn and Hall concluded that "[t]hese 1,3-disubstituted dienes are too reactive toward polymerization to handle readily." And that "[t]he new dienes are highly polymerizable and the syntheses are difficult to carry out in substantial quantities. These dienes are more reactive toward polymerization than any other mono- or di-electronegatively substituted 1,3-butadienes reported to date." Examples of these butadienes include

Only the second and third compounds listed above were reported by Ahn and Hall to have been isolated.

Absent from the published literature, however, are methods of using substituted activated methylene reagents to form electron deficient 1,3- or 1,3,3-substituted butadienes, which would be useful in the formation of curable compositions prepared therefrom. Until now.

SUMMARY OF THE INVENTION

The present invention provides substituted activated methylene reagents and methods of using such reagents to form electron deficient olefins, such as 1,3- or 1,3,3-substituted butadienes.

More specifically, in one aspect, the invention provides compounds comprising structure A:

A wherein:
X and X' are each independently an electron withdrawing group;
L is a leaving group;
W is H, alkyl, cycloaliphatic or aryl; and
R' is H, alkyl, or a cation selected from alkali metal cations, ammonium cations or phosphonium cations.

The invention also provides compounds comprising structure B:

B wherein:
X and X' are each independently an electron withdrawing group;
W is H, alkyl, cycloaliphatic or aryl; and
R' is H, alkyl, or a cation selected from alkali metal cations, ammonium cations or phosphonium cations.

The invention further provides compounds comprising structure C:

C wherein:
X" and X''' are each independently an electron withdrawing group;
L is a leaving group;
W is H, alkyl, cycloaliphatic or aryl;
R" is a spacer, such as an alkylene, with or without substitution or interruption by heteroatoms; and
n is 2-4.

The invention still further provides compounds comprising structure E:

E wherein:
X" and X''' are each independently an electron withdrawing group;
W is H, alkyl, cycloaliphatic or aryl;
R" is a spacer, such as an alkylene, with or without substitution or interruption by heteroatoms; and
n is 2-4.

In another aspect, the invention provides a method of making compounds of structure B:

B wherein:
X and X' are each independently an electron withdrawing group;
R' is H, alkyl, or a cation selected from alkali metal cations, ammonium cations or phosphonium cations; and W is H, alkyl, cycloaliphatic or aryl, comprising the steps of:
(a) providing compounds of structure I:

wherein:
X and X" are each independently an electron withdrawing group;
L is a leaving group; and
W is H, alkyl, cycloaliphatic or aryl; and
(b) exposing the compounds of structure I to either (i) conditions appropriate to form compounds of structure A or (ii) conditions appropriate to form compounds of structure B.

The invention in this aspect also provides a method of making compounds of structure C wherein:
X" and X"' are each independently an electron withdrawing group;
L is a leaving group;
W is H, alkyl, cycloaliphatic or aryl;
R" is a spacer, such as an alkylene, with or without substitution or interruption by heteroatoms; and
n is 2-4,
comprising the steps of:
(a) providing compounds of structure I:

wherein:
X and X" are each independently an electron withdrawing group;
L is a leaving group; and
W is H, alkyl, cycloaliphatic or aryl;
(b) exposing the compounds of structure I to (i) conditions appropriate to form compounds of structure A wherein R' is H or (ii) conditions appropriate to form compounds of structure C; and
(c) exposing the compound formed in step (b)(i) above to conditions appropriate to form compounds of structure C.

The invention in this aspect further provides a method of making compounds of structure F:

wherein:
X, X', X" and X"' are each independently electron withdrawing groups;
W is H, alkyl, cycloaliphatic or aryl; and
R" is a spacer, such as an alkylene, with or without substitution or interruption by heteroatom, comprising the steps of:
(a) providing compounds of structure I:

wherein:
X and X" are each independently an electron withdrawing group;
L is a leaving group; and
W is H, alkyl, cycloaliphatic or aryl; and
(b) exposing the compounds of structure I to either (i) conditions appropriate to form compounds of structure A or (ii) conditions appropriate to form compounds of structure B; and
(c) exposing the compounds formed in step (b) shown to conditions appropriate to form compounds of structure F.

DETAILED DESCRIPTION OF THE INVENTION

As noted above, the present invention provides substituted activated methylene reagents and methods of using such reagents to form electron deficient olefins, such as 1,3- or 1,3,3-substituted butadienes.

More specifically, in one aspect, the invention provides compounds comprising structure A:

A wherein:
X and X' are each independently an electron withdrawing group;
L is a leaving group;
W is H, alkyl, cycloaliphatic or aryl; and
R' is H, alkyl, or a cation selected from alkali metal cations, ammonium cations or phosphonium cations.

The invention also provides compounds comprising structure B:

B wherein:
X and X' are each independently an electron withdrawing group;
W is H, alkyl, cycloaliphatic or aryl; and
R' is H, alkyl, or a cation selected from alkali metal cations, ammonium cations or phosphonium cations.

The invention further provides compounds comprising structure C:

C wherein:
X" and X'" are each independently an electron withdrawing group;
L is a leaving group;
W is H, alkyl, cycloaliphatic or aryl;
R" is a spacer, such as an alkylene, with or without substitution or interruption by heteroatoms; and
n is 2-4.

Here, within structure C are compounds embraced by structure D:

D wherein:
X, X', X" and X'" are each independently an electron withdrawing group;
L is a leaving group;
W is H, alkyl, cycloaliphatic or aryl;
R" is a spacer, such as an alkylene, with or without substitution or interruption by heteroatoms; and
n is 2-4.

The invention still further provides compounds comprising structure E:

E wherein:
X" and X'" are each independently an electron withdrawing group;
W is H, alkyl, cycloaliphatic or aryl;
R" is a spacer, such as an alkylene, with or without substitution or interruption by heteroatoms; and
n is 2-4.

Here, within structure E are compounds embraced by structure F:

F wherein:
X, X', X" and X'" are each independently an electron withdrawing group;
W is H, alkyl, cycloaliphatic or aryl; and
R" is a spacer, such as an alkylene, with or without substitution or interruption by heteroatoms. Examples of the spacer include alkylene, such as methylene, ethylene, propylenes and butylenes, cycloalkylene, such as cyclopentylenes and cyclohexylenes, alkylene oxides, and arylene, such as phenylenes.

In these structures, X, X', X" and X'" are each independently electron withdrawing groups selected from CN, $CO_2R$, $CO_2H$, COCl, COR, $COPO(OR)_2$, $COPOR_2$, $SO_2R$, $SO_3R$ or $NO_2$, wherein R is $C_{1-4}$.

L is a leaving group selected from halogens, amines, or phosphonates.

An example of a compound embraced by structure A is

Examples of compounds embraced by structure B include

An example of a compound embraced by structure C is

An example of a compound embraced by structure D is

Examples of compounds embraced by structure F include

In another aspect, the invention provides a method of making compounds of structure B:

wherein:

X and X' are each independently an electron withdrawing group;

R' is H, alkyl, or a cation selected from alkali metal cations, ammonium cations or phosphonium cations; and W is H, alkyl, cycloaliphatic or aryl, comprising the steps of:

(a) providing compounds of structure I:

wherein:

X and X" are each independently an electron withdrawing group;

L is a leaving group; and

W is H, alkyl, cycloaliphatic or aryl; and (b) exposing the compounds of structure I to either (i) conditions appropriate to form compounds of structure A or (ii) conditions appropriate to form compounds of structure B.

The invention in this aspect also provides a method of making compounds of structure C wherein:

X" and X'" are each independently an electron withdrawing group;

L is a leaving group;

W is H, alkyl, cycloaliphatic or aryl;

R" is a spacer, such as an alkylene, with or without substitution or interruption by heteroatoms; and n is 2-4, comprising the steps of:

(a) providing compounds of structure I:

wherein:

X and X" are each independently an electron withdrawing group;

L is a leaving group; and

W is H, alkyl, cycloaliphatic or aryl;

(b) exposing the compounds of structure I to (i) conditions appropriate to form compounds of structure A wherein R' is H or (ii) conditions appropriate to form compounds of structure C; and (c) optionally, exposing the compound formed in step (b)(i) above to conditions appropriate to form compounds of structure C.

The conditions of step (c) involve providing R"-(OH)$_n$, wherein R" is a spacer and n is 2-4 so as to form n functional esters in compounds of structure C. Representative hydroxyl compounds include compounds where the spacer, R" includes alkylenes, alkylene oxides, or siloxanes. For instance, butylenes or triethylene glycol.

The invention in this aspect further provides a method of making compounds of structure F:

wherein:

X, X', X" and X''' are each independently selected from electron withdrawing groups;

W is H, alkyl, cycloaliphatic or aryl; and

R" is a spacer, such as an alkylene, with or without substitution or interruption by heteroatom, comprising the steps of:

(a) providing compounds of structure I:

wherein:

X and X" are each independently an electron withdrawing group;

L is a leaving group; and

W is H, alkyl, cycloaliphatic or aryl; and (b) exposing the compounds of structure I to either (i) conditions appropriate to form compounds of structure A or (ii) conditions appropriate to form compounds of structure B; and (c) exposing the compounds formed in step (b) shown to conditions appropriate to form compounds of structure F.

Desirably, compounds of structure I include

In these methods, where compounds of structure A have R' as H, structure A may be esterified under appropriate conditions.

In these methods, compounds of structure I may be reacted with a basic compound at elevated temperatures to form structure A or C, as appropriate.

The basic compound used in these methods may be selected from morpholine, piperidine, pyrrolidine, piperazine, 1,3,3 trimethyl 6-azabicyclo[3,2,1]octane, thiazolidine, homopiperazine, aziridine, 1,4-diazabicylo[2.2.2]octane, 1-amino-4-methylpiperazine, lithium bases (such as lithium N-isopropylcyclohexylamide), and 3-pyrroline.

In these methods, where an elevated temperature condition is chosen that condition should be above 100° C.

By these methods compounds of the present invention may be made. In addition, known compounds may be made as well by these methods or by modest variations of these methods. For instance, see K-D. Ahn and H. K. Hall, "Synthesis and Polymerization of the Four 1,3-Di(Cyano and/or Carbomethoxy)-Substituted Butadienes", *J. Polym. Sci.: Polym. Chem. Ed.*, 19, 629-44 (1981). The present invention also provides curable compositions prepared from the inventive compounds, together with a stabilizer package comprising at least one of a free radical stabilizer and an anionic stabilizer; and optionally, one or more additives selected from cure accelerators, thickeners, thixotropes, tougheners, thermal resistance-conferring agents, or plasticizers.

Moreover, the curable compositions may include one or more radically curable monomers, chief among such monomers are (meth)acrylates or (meth)acrylate-functionalized compounds optionally together with a radical initiator For instance, the inventive compounds may be used in a curable composition that may include a cyanoacrylate and/or a (meth)acrylate.

The following examples are intended to illustrate but in no way limit the present invention.

EXAMPLES

Example 1

Figure 1:
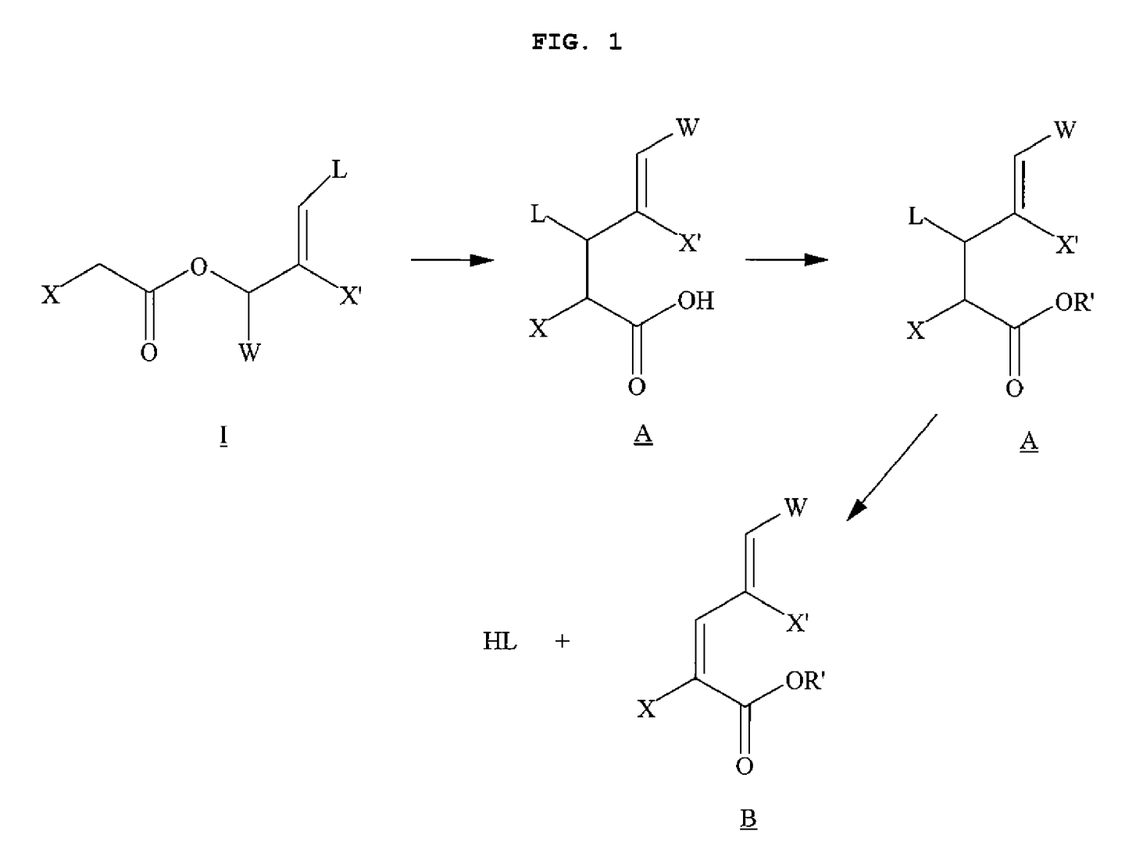
FIG. 1 depicts a synthetic scheme by which a 1,3,3-substituted electron deficient butadiene compound may be prepared according to the present invention from a substituted activated methylene reagent.
Figure 2:
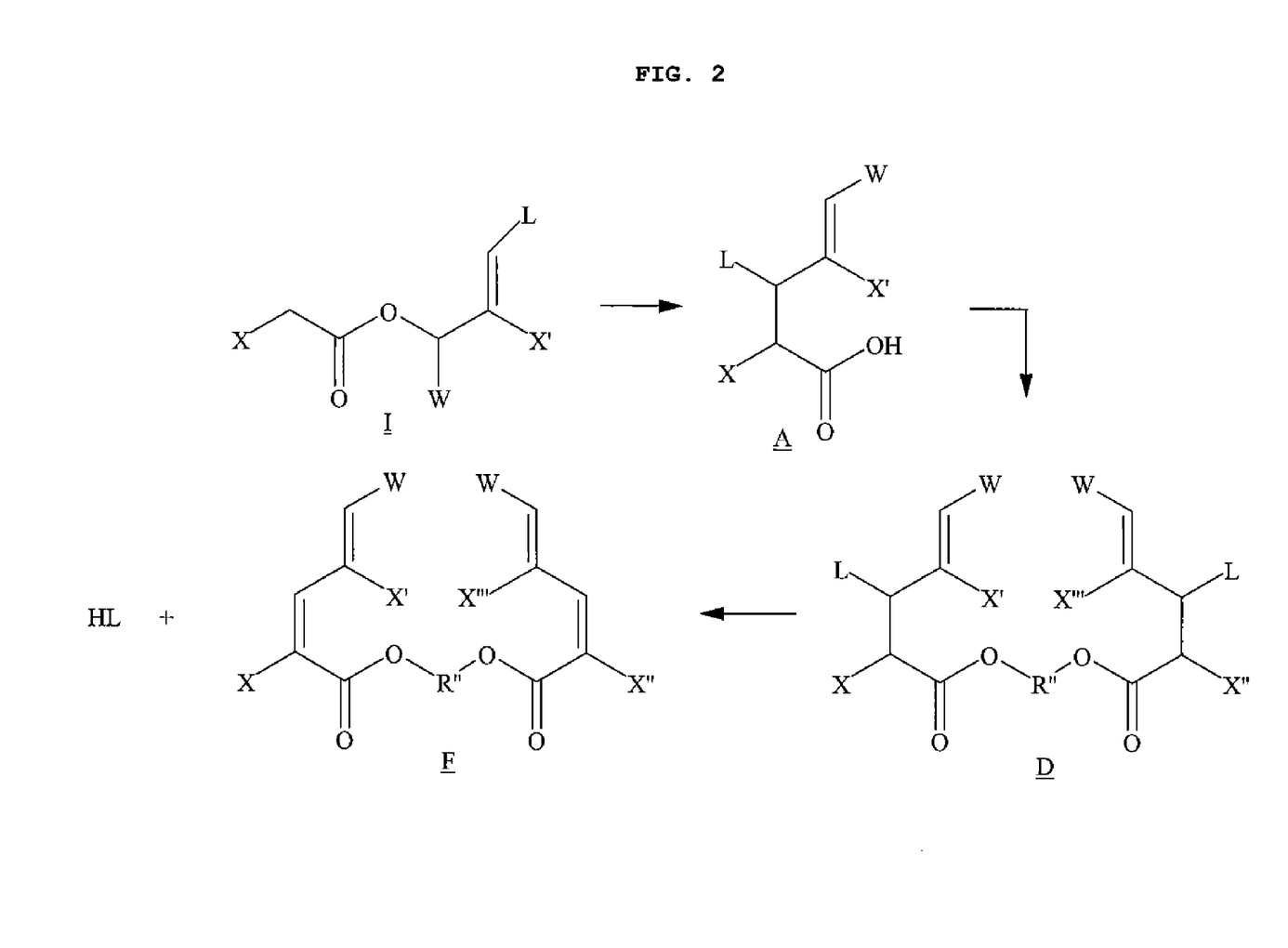
FIG. 2 depicts a synthetic scheme by which a 1,3,3-substituted electron deficient butadiene compound may be prepared according to the present invention from a substituted activated methylene reagent.
Figure 3:
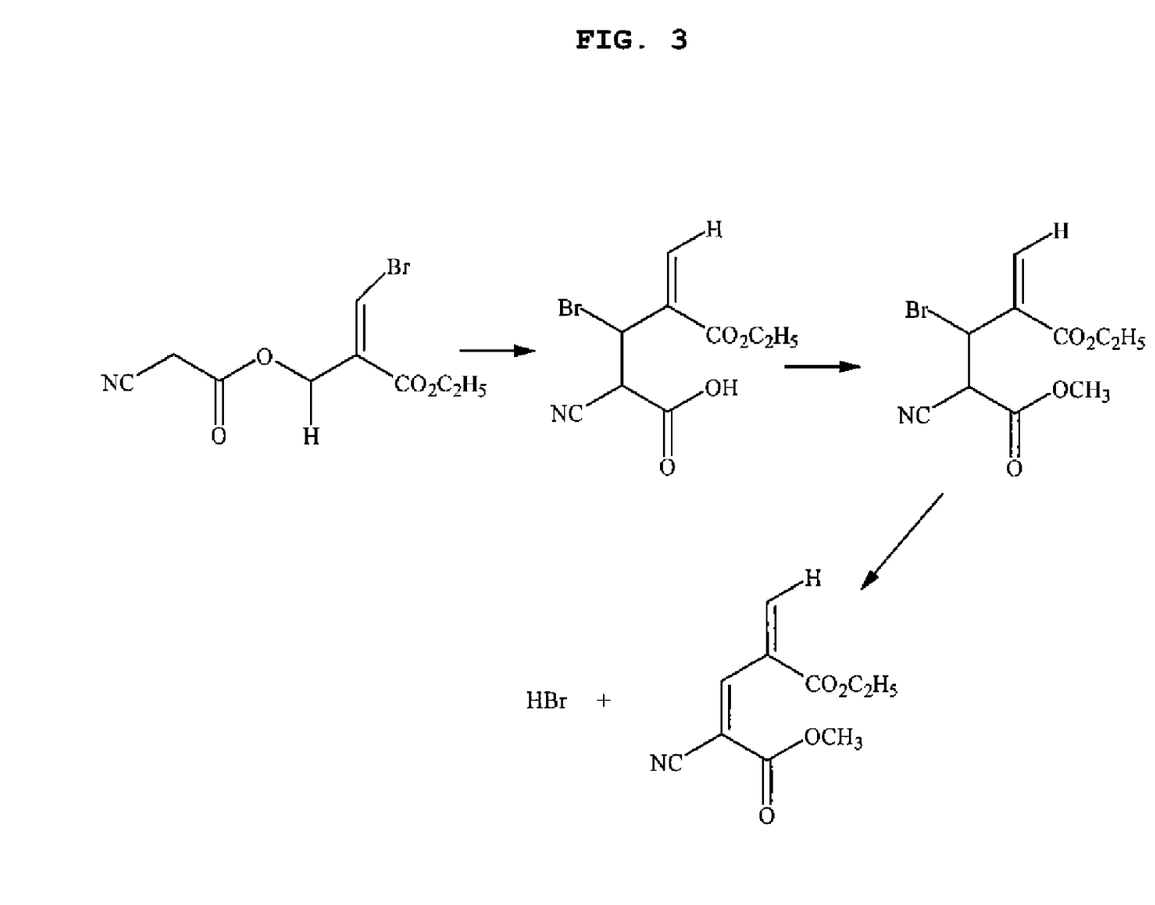
FIG. 3 depicts a synthetic scheme by which a 1,3,3-substituted electron deficient butadiene compound may be prepared according to the present invention from a substituted activated methylene reagent.
Figure 4:
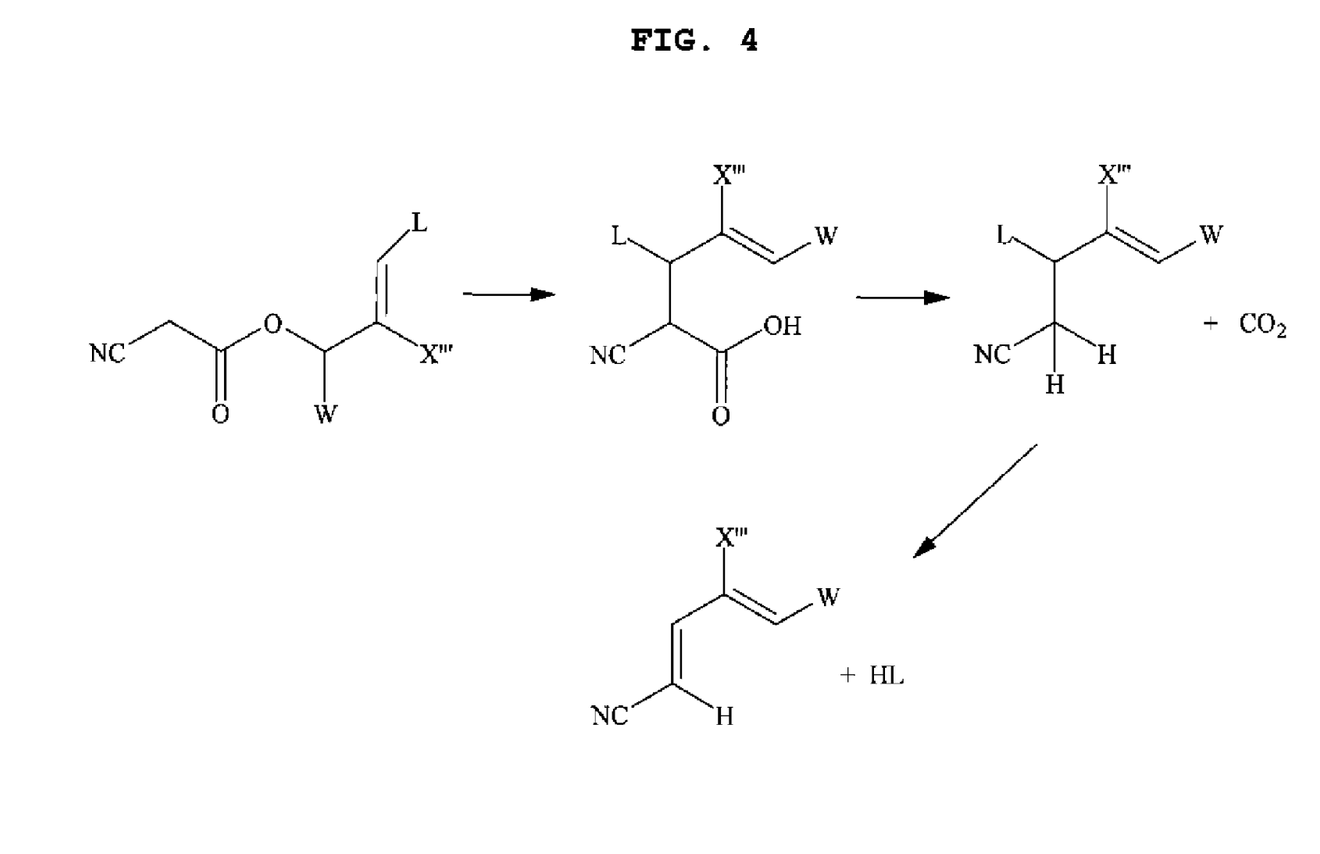
FIG. 4 depicts a synthetic scheme representative of a method of the present invention by which a 1,3-substituted electron deficient butadiene compound may be prepared from a substituted active methylene compound.
Figure 5:
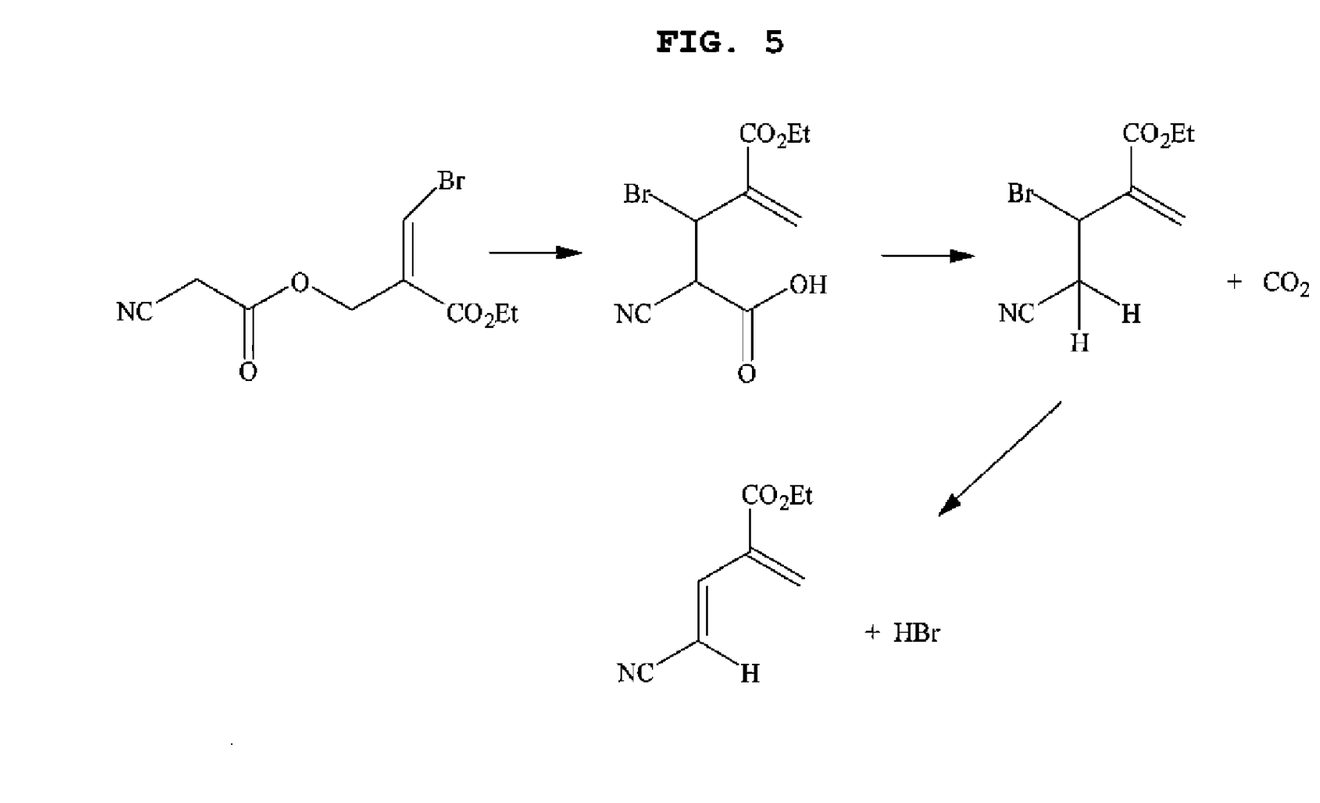
FIG. 5 depicts a synthetic scheme representative of a method of the present invention by which a 1,3-substituted electron deficient butadiene compound may be prepared from a substituted active methylene compound.

With reference to FIG. 1, the first generic compound in the synthetic sequence (structure I) is prepared where X is CN, W is H, X' is CO$_2$Et, and L is H.

More specifically, in a 1 liter three-necked flask, alpha (hydroxymethyl)ethylacrylate (260.0 g, 2.0 mol) and 1.1 equivalent of cyanoacetic acid (187.0 g, 2.2 mol) were suspended in toluene (420 mL) with hydroquinone (0.8 g). The mixture was heated at a temperature of 90° C. until the cyanoacetic acid melted, at which point a catalytic amount (two drops) of sulfuric acid was added. The reaction mixture was stirred with heating at a temperature of 125° C. with a Dean-Stark apparatus attached to remove the water.

The reaction mixture was washed with dilute aqueous sodium bicarbonate to remove excess cyanoacetic acid, then with dilute hydrochloric acid and finally with brine. The solvent (toluene) was removed under reduced pressure and the residue with an added 1 g of hydroquinone was distilled (b.p. 130° C. at 0.2 mm Hg) to furnish 197 g of the final product in a yield of 51%. Spectral confirmation is given below.

$^1$H-NMR (60 MHz, CDCl$_3$): δ=1.32 (t, 3H), 3.49 (s, 2H), 4.24 (q, 2H), 4.92 (s, 2H), 5.90 (s, 1H), 6.41 (s, 1H) ppm.

FT-IR (film): 2983.1, 2929.4, 2259.3, 1750.8, 1712.7, 1638.8, 1447.4, 1395.9, 1367.9, 1336.0, 1309.1, 1270.0, 1176.4, 1152.9, 1023.5, 957.7, 879.3, 859.1, 815.9 cm$^{-1}$.

Example 2

To the compound obtained from Example 1 (10.0 g, 51 mmol) was added 5% by weight of DABCO (0.50 g, 4.5 mmol) in a 50 mL one-necked-flask and the mixture was heated at a temperature of 100° C. for a period of time 6 hours under vigorous stirring. The crude oil obtained showed a conversion of about 80% by the $^1$H-NMR attributed to rearrangement of the starting material.

A sample of 1.6 g (7.7 mmol) of the crude product from the preceding paragraph was dissolved in chloroform (10 mL) and washed with 1.2 N HCl (10 mL) to remove the DABCO. After evaporating the solvent (chloroform) the organic layer afforded 0.63 g (3.2 mmol) of the product in a 41% yield. This product represents the second generic compound (structure II) in the synthetic scheme of FIG. 1. Spectral confirmation is given below.

$^1$H-NMR (60 MHz, DMSO-d$_6$): δ=1.31 (t, 3H), 2.95 (bs, 2H), 3.88 (s, 1H), 4.25 (q, 2H), 5.93 (s, 1H), 6.35 (s, 1H), 10.83 (bs, 1H) ppm.

FT-IR (film): 3162.3, 3023.4, 2984.1, 2937.6, 2904.9, 2177.5, 1750.0, 1712.0, 1630.3, 1444.7, 1370.7, 1303.1, 1274.9, 1175.1, 1151.9, 1095.9, 1021.9, 958.7, 815.8, 751.1 cm$^{-1}$.

Example 3

In a 100 mL three-necked-flask the crude product from Example 2 (2.2 g, 11.1 mmol) was dissolved in dry dichloromethane (30 mL) with an equivalent of absolute ethanol (0.65 mL). Then, 1,3-dicyclohexylcarbodiimide (2.28 g, 11.1 mmol) dissolved in dry dichloromethane (10 mL) was added dropwise over a half hour period of time, cooling the reaction with an ice bath. The reaction was allowed to continue at room temperature overnight. A white precipitate (dicyclohexylurea) was observed to form and was thereafter filtered away, leaving an organic solution. The solution was washed twice with brine, and the solvent was removed under reduced pressure to afford 2.8 g of crude oil in a quantitative yield. Distillation (b.p.=150° C. under a vacuum of 0.2 mm Hg) afforded the third compound in the synthetic sequence of FIG. 1. Spectral confirmation is given below.

$^1$H-NMR (60 MHz, DMSO-d$_6$): δ=1.31 (t, 6H), 3.03 (bs, 2H), 4.04 (s, 1H), 4.23 (q, 4H), 5.91 (s, 1H), 6.37 (s, 1H) ppm.

FT-IR (film): 2983.9, 2941.7, 2904.9, 2868.1, 2242.9, 1742.8, 1713.0, 1630.0, 1513.3, 1444.4, 1369.8, 1279.4, 1214.2, 1175.3, 1151.8, 1113.0, 1095.2, 1022.4, 960.8, 856.5, 818.8 cm$^{-1}$.

Example 4

In a 100 mL three-necked-flask the product from Example 2 (2.2 g, 11.1 mmol) was dissolved in dry dichloromethane (30 mL) with an equivalent of diol (0.65 mL). Then, 1,3-dicyclohexylcarbodiimide (2.28 g, 11.1 mmol) dissolved in dry dichloromethane (10 mL) was added dropwise over a half hour period of time, cooling the reaction with an ice bath. The reaction was allowed to continue at room temperature overnight. A white precipitate (dicyclohexylurea) was observed to form and was shortly thereafter filtered away, leaving an organic solution. The solution was washed twice with brine, and the solvent was removed under reduced pressure to afford 2.8 g of crude oil in a quantitative yield. Distillation (b.p. 150° C. under 0.2 mm Hg) afforded the third compound in the synthetic sequence of FIG. 1.

Example 5

The synthetic procedure of J. Villieras et al., *Synthesis,* 928 (1982) was followed here.

In 1 liter three-necked-flask, alpha(hydroxymethyl)ethylacrylate (68 g, 0.52 mol) was dissolved in dry diethyl ether (0.5 L) and cooled at a temperature of 0° C. with an ice bath. Phosphorus tribromide (68 g, 0.24 mol) was added dropwise under vigorous stirring, then the mixture was allowed to rise at room temperature and the reaction was continued for 3 hours. The organic layer was added dropwise to a 300 mL of stirring water with ice, then extracted three times with ethyl acetate (100 mL). The combined organic layers were washed twice with brine (100 mL) and dried over anhydrous sodium sulphate. After the removal of solvent (ethyl acetate), the crude oil was distilled (b.p.=69° C. under a vacuum of 7.5 mm Hg) to afford 90 g of the final product in a yield of 89%. Spectral confirmation is given below.

$^1$H-NMR (60 MHz, CDCl$_3$): δ=1.33 (t, 3H), 4.18 (s, 2H), 4.25 (q, 2H), 5.93 (s, 1H), 6.31 (s, 1H).

FT-IR (film): 2081.6, 2933.5, 2904.9, 2872.2, 1716.0, 1628.5, 1444.3, 1398.0, 1368.8, 1328.4, 1308.8, 1221.2, 1181.8, 1115.5, 1022.1, 956.3, 855.9, 808.9 cm$^{-1}$.

What is claimed is:

1. Compounds comprising structure A:

wherein:
wherein X and X' are each independently an electron withdrawing group selected from CN, CO$_2$R, CO$_2$H, COCl, COR, COPO(OR)$_2$, COPOR$_2$, SO$_2$R, SO$_3$R or NO$_2$, where R is C1-4;
L is a leaving group;
W is H, alkyl, cycloaliphatic or aryl; and
R' is H, alkyl, or a cation selected from the group consisting of alkali metal cations, ammonium cations and phosphonium cations.

2. Compounds comprising structure C:

wherein:
wherein X" and X"' are each independently an electron withdrawing group selected from CN, CO$_2$R, CO$_2$H, COCl, COR, COPO(OR)$_2$, COPOR$_2$, SO$_2$R, SO$_3$R or NO$_2$, where R is C1-4;

L is a leaving group;
W is H, alkyl, cycloaliphatic or aryl;
R" is an alkylene with or without substitution or interruption by heteroatom; and
n is 2-4.

3. Compounds of claim 2, embraced by structure D:

D wherein:
wherein X, X', X" and X'" are each independently an electron withdrawing group selected from CN, $CO_2R$, $CO_2H$, COCl, COR, $COPO(OR)_2$, $COPOR_2$, $SO_2R$, $SO_3R$ or $NO_2$, where R is C1-4;
L is a leaving group;
W is H, alkyl, cycloaliphatic or aryl;
R" is an alkylene with or without substitution or interruption by heteroatom;
n is 2-4.

4. A method of making compounds of structure C

C wherein:
wherein X" and X'" are each independently an electron withdrawing group selected from CN, $CO_2R$, $CO_2H$, COCl, COR, $COPO(OR)_2$, $COPOR_2$, $SO_2R$, $SO_3R$ or $NO_2$, where R is C1-4;
L is a leaving group;
W is H, alkyl, cycloaliphatic or aryl;
R" is a spacer; and
n is 2-4,
comprising the steps of:
(a) providing compounds of structure I:

I wherein:
X and X" are each independently an electron withdrawing group;
L is a leaving group; and
W is H, alkyl, cycloaliphatic or aryl;
(b) exposing the compounds of structure I to (i) conditions appropriate to form compounds of structure A as defined in claim 1 wherein R' is H or (ii) conditions appropriate to form compounds of structure C as defined in claim 2; and
(c) optionally, exposing the compound formed in step (b)(i) above to conditions appropriate to form compounds of structure C.

5. The method of claim 4, wherein the conditions of step (c) involve providing $R"-(OH)_n$, wherein R" is a spacer and n is 2-4 so as to form n functional esters in compounds of structure C.

6. The method of claim 4, wherein structure I is

7. The method of claim 5, wherein structure I is

8. The method of claim 4, wherein structure I is reacted with a basic compound at elevated temperatures to form structure C.

9. The method of claim 4, wherein when in structure A R' is H, structure A is esterified under appropriate conditions.

10. The method of claim 8, wherein the basic compound is a member selected from the group consisting of morpholine, piperidine, pyrrolidine, piperazine, 1,3,3 trimethyl 6-azabicyclo[3,2,1]octane, thiazolidine, homopiperazine, aziridine, 1,4-diazabicylo[2.2.2]octane, 1-amino-4-methylpiperazine, lithium bases, and 3-pyrroline.

11. The method of claim 8, wherein the elevated temperature conditions are above 100° C.

12. Compounds according to claim 1, wherein L is selected from the group consisting of halogen, amine, and phosphonate.

* * * * *